United States Patent
Nagalla

(10) Patent No.: US 9,383,370 B2
(45) Date of Patent: *Jul. 5, 2016

(54) MATERNAL BIOMARKERS FOR GESTATIONAL DIABETES

(71) Applicant: DiabetOmics, LLC, Hillsboro, OR (US)

(72) Inventor: Srinivasa R. Nagalla, Hillsboro, OR (US)

(73) Assignee: Diabetomics, Inc., Hillsboro, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/516,383

(22) Filed: Oct. 16, 2014

(65) Prior Publication Data

US 2015/0037822 A1  Feb. 5, 2015

Related U.S. Application Data

(60) Continuation of application No. 14/085,974, filed on Nov. 21, 2013, now Pat. No. 8,975,034, which is a division of application No. 13/792,844, filed on Mar. 11, 2013, now Pat. No. 8,852,873.

(60) Provisional application No. 61/623,690, filed on Apr. 13, 2012.

(51) Int. Cl.
*G01N 33/53* (2006.01)
*G01N 33/68* (2006.01)
*G01N 33/76* (2006.01)
*G01N 33/74* (2006.01)

(52) U.S. Cl.
CPC .............. *G01N 33/689* (2013.01); *G01N 33/74* (2013.01); *G01N 33/76* (2013.01); *G01N 2333/471* (2013.01); *G01N 2333/78* (2013.01); *G01N 2800/042* (2013.01); *G01N 2800/368* (2013.01); *G01N 2800/60* (2013.01)

(58) Field of Classification Search
None
See application file for complete search history.

(56) References Cited

U.S. PATENT DOCUMENTS

| | | |
|---|---|---|
| 4,855,242 A | 8/1989 | Soeldner |
| 4,929,543 A | 5/1990 | Kientsch-Engel et al. |
| 5,200,318 A | 4/1993 | Rabin et al. |
| 5,512,447 A | 4/1996 | Baekkeskov et al. |
| 5,547,847 A | 8/1996 | Hagopian et al. |
| 5,561,049 A | 10/1996 | Vold et al. |
| 5,645,998 A | 7/1997 | Atkinson et al. |
| 5,670,377 A | 9/1997 | Peterson et al. |
| 5,674,692 A | 10/1997 | Baekkeskov et al. |
| 5,770,381 A | 6/1998 | MacKay et al. |
| 5,792,620 A | 8/1998 | Lernmark et al. |
| 5,846,740 A | 12/1998 | Tobin et al. |
| 5,849,506 A | 12/1998 | Baekkeskov et al. |
| 5,968,757 A | 10/1999 | Powers |
| 5,989,551 A | 11/1999 | Maclaren et al. |
| 6,004,759 A | 12/1999 | Johnson et al. |
| 6,165,738 A | 12/2000 | Mackay et al. |
| 6,214,568 B1 | 4/2001 | Endl et al. |
| 6,300,089 B1 | 10/2001 | Atkinson et al. |
| 6,303,325 B1 | 10/2001 | Mehta et al. |
| 6,316,209 B1 | 11/2001 | Baekkeskov et al. |
| 6,391,651 B1 | 5/2002 | Maclaren et al. |
| 6,967,108 B1 | 11/2005 | Endl et al. |
| 7,332,349 B2 | 2/2008 | Yang et al. |
| 7,368,542 B2 | 5/2008 | McIntyre |
| 7,718,386 B1 | 5/2010 | Baekkeskov et al. |
| 7,851,164 B2 | 12/2010 | Seve et al. |
| 8,334,146 B2 | 12/2012 | McIntyre |
| 2002/0131963 A1 | 9/2002 | Baekkeskov et al. |
| 2003/0166067 A1 | 9/2003 | Kindsvogel et al. |
| 2004/0048274 A1 | 3/2004 | Breindahl |
| 2004/0142387 A1 | 7/2004 | Lernmark et al. |
| 2005/0130245 A1 | 6/2005 | Houle et al. |
| 2005/0260681 A1 | 11/2005 | McIntyre |
| 2006/0024725 A1 | 2/2006 | Hussa et al. |

(Continued)

FOREIGN PATENT DOCUMENTS

| | | |
|---|---|---|
| CN | 101416063 A | 4/2009 |
| CN | 101646781 A | 2/2010 |
| CN | 102308002 A | 1/2012 |
| WO | 2005-017192 A2 | 2/2005 |
| WO | 2007-062789 A1 | 6/2007 |
| WO | 2009-045403 A2 | 4/2009 |
| WO | 2009/097579 A1 | 8/2009 |

OTHER PUBLICATIONS

Hampel et al (J. Immu Methods 1999 vol. 224, p. 31-42).*
Sato et al. (JBC 1992 vol. 267, p. 6983-6990).*
Olden et al. PNAS 1979 vol. 76, p. 3343-3347.*
Pledger, D. R. et al., "Human Placental Lactogen and Pregnancy-specific Beta1-glycoprotein in Pregnant Diabetic Women," British Journal of Obstetrics and Gynaecology, Oct. 1982, vol. 89, pp. 827-830.

(Continued)

*Primary Examiner* — Jacob Cheu
(74) *Attorney, Agent, or Firm* — Schwabe Williamson & Wyatt

(57) ABSTRACT

Embodiments herein relate to the field of screening tools for fetal/maternal wellness, and, more specifically, to biomarkers for gestational diabetes. In various embodiments, the methods may provide non-invasive and minimally-invasive screening tools for gestational diabetes that involve detection of changes in a proteomic profile of a test sample relative to a reference sample. In particular embodiments, the method may include determining whether a proteomic profile of a test sample from the subject includes at least one expression signature characteristic of gestational diabetes, wherein the proteomic profile comprises information on the expression of glycosylated fibronectin and glycosylated PSG, for example information on levels of fibronectin-SNA or a fibronectin-antibody complex, and PSG-AAL or a PSG-antibody complex. In some embodiments, the proteomic profile may also include information on the expression of adiponectin, sex hormone binding globulin (SHBG), C-reactive protein (CRP), a ratio of human chorionic gonadotropin (hCG) to placental lactogen, or a combination thereof.

24 Claims, 10 Drawing Sheets

(56) References Cited

U.S. PATENT DOCUMENTS

| | | |
|---|---|---|
| 2007/0026465 A1 | 2/2007 | Fierabracci et al. |
| 2007/0224638 A1 | 9/2007 | Melanitou-McClymont |
| 2009/0111738 A1 | 4/2009 | Clark et al. |
| 2009/0197286 A1 | 8/2009 | Karin et al. |
| 2010/0016173 A1 | 1/2010 | Nagalla et al. |
| 2010/0120629 A1 | 5/2010 | Ellis et al. |
| 2010/0143374 A1 | 6/2010 | Hutton et al. |
| 2010/0330110 A1 | 12/2010 | Robinson et al. |
| 2011/0052569 A1 | 3/2011 | Hampe et al. |
| 2011/0059904 A1 | 3/2011 | Sharma et al. |
| 2011/0244486 A1 | 10/2011 | Perego et al. |
| 2011/0318389 A1 | 12/2011 | Czernichow et al. |
| 2012/0015383 A1 | 1/2012 | Park et al. |
| 2012/0077709 A1 | 3/2012 | Ellis et al. |
| 2012/0301491 A1 | 11/2012 | Nilsson et al. |
| 2013/0011860 A1 | 1/2013 | Eisenbarth et al. |
| 2013/0045887 A1 | 2/2013 | Zhang et al. |

OTHER PUBLICATIONS

Tsao, Shyn-Ming et al., "Meticillin-resistant *Staphylococcus aureus* Infection in Diabetic Mice Enhanced Inflammation and Coagulation," Journal of Medical Microbiology, 2006, vol. 55, pp. 379-385.

Yeu, Tingting et al., "The Prevalence and Nature of Glycan Alterations on Specific Proteins in Pancreatic Cancer Ptients Revealed Using Antibody-Lectin Sandwich Arrays," Molecular & Cellular Proteomics, 2009, 12 pages.

\* cited by examiner

MATERNAL BIOMARKERS FOR GESTATIONAL DIABETES

CROSS REFERENCE TO RELATED APPLICATIONS

The present application is a continuation of U.S. patent application Ser. No. 14/085,974, filed Nov. 21, 2013, entitled "MATERNAL BIOMARKERS FOR GESTATIONAL DIABETES," which, in turn, was a divisional of U.S. patent application Ser. No. 13/792,844, filed Mar. 11, 2013, entitled "MATERNAL BIOMARKERS FOR GESTATIONAL DIABETES," which claims priority to U.S. Provisional Patent Application No. 61/623,690, filed Apr. 13, 2012, entitled "MATERNAL BIOMARKERS FOR GESTATIONAL DIABETES," the entire disclosure of which is hereby incorporated by reference in its entirety.

TECHNICAL FIELD

Embodiments herein relate to the field of screening tools for fetal/maternal wellness, and, more specifically, to biomarkers for gestational diabetes.

BACKGROUND

The rates of obesity and diabetes have increased rapidly over the last 20 years, both in the United States and globally. The incidence of gestational diabetes mellitus (GDM) is also increasing, paralleling the overall rise in obesity and type-2 diabetes. The adoption of new diagnostic criteria based upon the recent Hyperglycemia and Adverse Pregnancy Outcomes (HAPO) study is expected to increase the prevalence of GDM to about 18% of all pregnancies. In light of the fact that 80-90% of women with GDM can be managed with lifestyle therapy alone, universal screening for GDM is increasingly considered justified.

GDM is a serious complication of pregnancy that can increase the risk of a number of maternal-fetal disorders, including macrosomia, shoulder dystocia or birth injury, premature delivery, and preeclampsia. In addition to the increased risk of complications associated with gestation and delivery, there are also serious post-natal complications associated with GDM. For instance, 5 to 10% of women with GDM are found to have diabetes immediately after pregnancy, and women who have had GDM have a 10-fold higher chance of developing diabetes within the next 10-20 years. Children of mothers with GDM have an eight-fold greater risk of developing type-2 diabetes in later life. Thus, untreated GDM contributes to the overall diabetic population in both the short and long term.

Universal or even widespread GDM screening is hampered by the fact that the standard assessments of diabetes and pre-diabetes, such as fasting insulin/glucose and HbA1c, are not recommended for screening of GDM. Instead, the recommended parameter is an oral glucose tolerance test (OGTT), which is costly and invasive, requiring a hospital visit and multiple blood draws.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

DETAILED DESCRIPTION OF DISCLOSED EMBODIMENTS

Figure 1:
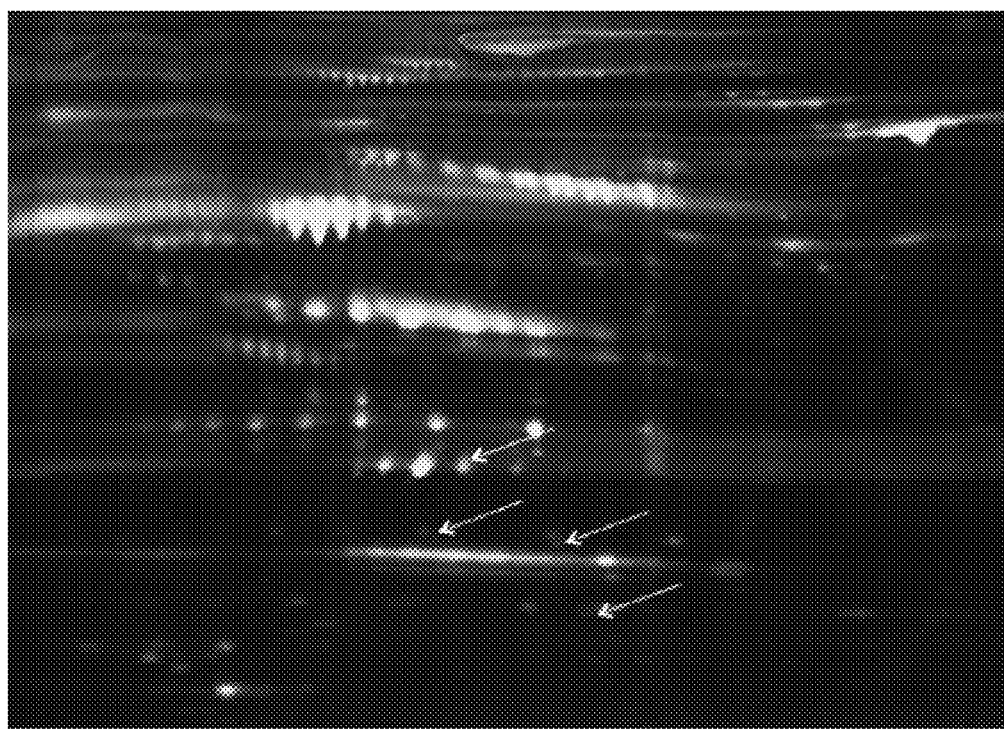
FIG. 1 illustrates a two-dimensional differential in-gel electrophoresis (2D-DIGE) analysis of control and GDM maternal serum samples, in which differentially abundant proteins (arrows) appear as red or green spots depending on the extent of under- or over-abundance, in accordance with various embodiments.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "NB" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

Disclosed herein in various embodiments are non-invasive and minimally invasive methods that may be used for the widespread screening for gestational diabetes. In various embodiments, the methods may include determining whether a proteomic profile of a test sample from a subject includes at least one expression signature characteristic of gestational diabetes, wherein the proteomic profile includes information on the expression of glycosylated fibronectin, for example by detection and/or quantification of glycosylated fibronectin, such by detecting/quantifying fibronectin-Sambucus nigra lectin (SNA) or a fibronectin-antibody complex, and/or by detecting and/or quantifying glycosylated pregnancy-specific glycoprotein (PSG), for example by detection/quantification of pregnancy specific glycoprotein-Aleuria aurantia lectin (PSG-AAL) or a PSG-antibody complex. In some embodiments, the proteomic profile may also include information on the expression of adiponectin, sex hormone binding globulin (SHBG), C-reactive protein (CRP), the ratio of human chorionic gonadotropin (hCG) to placental lactogen, or a combination thereof, such as two, three, or all four of adiponectin, SHBG, CRP, and the ratio of hCG to placental lactogen.

As used herein, the term "proteome" refers to a significant portion of the proteins in a biological sample at a given time. Generally speaking, the proteome is fundamentally different from a genome, in that while the genome is virtually static, the proteome continually changes in response to internal and external events. Thus, as used herein, the term "proteomic profile" refers to a representation of the expression pattern of a plurality of proteins in a biological sample, such as whole blood, plasma, serum, or saliva, at a given time. In various embodiments, a proteomic profile may, for example, be represented as a mass spectrum, but other representations based on any physicochemical or biochemical properties of the proteins are also included. Thus, a proteomic profile may, for example, be based on differences in the electrophoretic properties of proteins, as determined by two-dimensional polyacrylamide gel electrophoresis (2D-PAGE) or 2-dimensional differential in-gel electrophoresis (2D-DIGE), and may be represented, for example, as a plurality of spots in a two-dimensional electrophoresis gel. In various embodiments, differential expression profiles may have important diagnostic value, and protein spots may be detected and/or quantified, for example, by mass spectrometry, immunoblotting, ELISA assays, or protein microarrays. In various embodiments, proteins may be detected and/or quantified using lateral flow devices, such as for point-of-care use, as well as spot check colorimetric tests.

In various embodiments, a proteomic profile in accordance with the present disclosure may represent or contain information about at least 2, 3, 4, 5, 6, 7, 8, 9, 10, or even more proteins. As used herein, the term "expression signature" refers to a unique protein expression feature or motif within a proteomic profile of a biological sample (such as a test sample) that may differ from a proteomic profile of a corresponding reference sample (e.g., obtained from the same type of biological fluid) in a statistically significant manner. For example, in various embodiments, an "expression signature characteristic of gestational diabetes" may include a characteristic motif that differs from a proteomic profile of a normal reference sample, or it may share a characteristic motif with a proteomic profile from a gestational diabetes reference sample. In various embodiments, the expression signature may include an increase or decrease in the expression of two or more specific proteins, for example glycosylated fibronectin (for example, which may be detected as fibronectin-SNA or a fibronectin-antibody complex), glycosylated PSG (for example, which may be detected as PSG-AAL or a PSG-antibody complex), adiponectin, SHBG, and/or CRP, and/or it may include an increase or decrease in the ratio of expression of two or more specific proteins, such as the ratio of human chorionic gonadotropin (hCG) to placental lactogen. For each of these proteins, an exemplary GENBANK® Accession number is listed: human fibronectin, Genbank Accession No. P02751; human pregnancy-specific beta-1-glycoprotein 9, Genbank Accession No. gi:6093845; human sex hormone binding globulin, Genbank Accession No. gi:134907; human adiponectin, Genbank Accession No. gi:167077467; human choriogonadotropin subunit beta, Genbank Accession No. gi:116184; human glycoproteins hormone alpha chain, Genbank Accession No. gi:121312; human placental lactogen, Genbank Accession No. gi:190034; and human C-reactive protein, Genbank Accession No. gi:30224.

In some embodiments, the method includes detecting an increase, such as a statistically significant increase relative to a reference sample, such as at least a 10%, 15%, 25%, 50%, 75%, 100%, 150%, 200%, 250%, or even greater increase, in the expression of glycosylated fibronectin (which may be detected as, for example, fibronectin-SNA or a fibronectin-antibody complex) and glycosylated PSG (which may be detected as, for example, PSG-AAL or a PSG-antibody complex), or a statistically significant increase in the expression of glycosylated fibronectin (which may be detected as, for example, fibronectin-SNA or a fibronectin-antibody complex) and glycosylated PSG (which may be detected as, for example, PSG-AAL or a PSG-antibody complex), in addition to CRP and/or the ratio of hCG to placental lactogen. In some embodiments, the statistically significant increase in the expression of glycosylated fibronectin and PSG (e.g., fibronectin-SNA or a fibronectin-antibody complex and PSG-AAL or a PSG-antibody complex) also may be accompanied by a statistically significant decrease, such as at least a 10%, 15%, 25%, 50%, 75%, 100%, 150%, 200%, 250%, or even greater decrease, relative to the reference sample, in expression of adiponectin and/or SHBG. In particular embodiments, an expression signature characteristic of gestational diabetes may include a statistically significant increase in the expression of glycosylated fibronectin (e.g., detected as fibronectin-SNA or a fibronectin-antibody complex), glycosylated PSG (e.g., detected as PSG-AAL or a PSG-antibody complex), CRP, and the ratio of hCG to placental lactogen, in addition to a statistically significant decrease in expression of adiponectin and SHBG.

In various embodiments, if the reference sample is a normal or control reference sample, such as a sample from a subject who does not have gestational diabetes, and the proteomic profile of the test sample differs from the reference sample with regard to at least one expression signature characteristic of gestational diabetes, then the subject may be determined to have gestational diabetes. Conversely, if the test sample does not differ from the normal reference sample with regard to at least one expression signature characteristic of gestational diabetes, then the subject may be determined to not have gestational diabetes. In other embodiments, if the reference sample is a gestational diabetes reference sample, such as a sample from a subject who has gestational diabetes, and the proteomic profile of the test sample differs from the reference sample with regard to at least one expression signature characteristic of gestational diabetes, then the subject may be determined not to have gestational diabetes. Conversely, if the test sample does not differ from the gestational diabetes reference sample with regard to at least one expression signature characteristic of gestational diabetes, then the subject may be determined to have gestational diabetes. Some embodiments may use more than one reference sample, such as a normal reference sample and a gestational diabetes reference sample. Hence, the proteomic profile provides a diagnostic criterion for gestational diabetes. Statistical methods for determining if the abundance of a protein of interest is increased or decreased relative to a reference sample are well known in the art, and are described below.

In various embodiments, proteomic analysis of biological fluids, such as whole blood, saliva, or serum, may be performed using a variety of methods known to those of skill in the art. In various embodiments, in a direct comparative analysis, the reference sample and test sample may be treated exactly the same way, in order to correctly represent the relative abundance of proteins and obtain accurate results. For example, as discussed above, in various embodiments, the proteins present in the biological samples may be separated by 2D-gel electrophoresis according to their charge and molecular weight. For instance, the proteins may first be separated by their charge using isoelectric focusing (one-dimensional gel electrophoresis), for example using immobilized pH-gradient (IPG) strips, which are commercially available. In various embodiments, the second dimension may be an SDS-PAGE analysis, where the focused IPG strip may be used as the sample. After two-dimensional gel electrophoresis separation, proteins may then be visualized with conventional dyes, such as Coomassie Blue or silver staining, and imaged using known techniques and equipment, such as, for example Bio-Rad GS800 densitometer and PDQUEST™ software.

In some embodiments, individual spots may then be cut from the gel, de-stained, and subjected to tryptic digestion, allowing the peptide mixtures to be analyzed by mass spectrometry (MS). Alternatively, in some embodiments, the peptides may be separated, for example by capillary high pressure liquid chromatography (HPLC) and may be analyzed by MS either individually, or in pools. If desired, in some embodiments, the amino acid sequences of the peptide fragments and the proteins from which they derived may be determined. Although it is possible to identify and sequence all or some of the proteins present in a proteomic profile, this typically is not necessary for the diagnostic use of the proteomic profiles.

As discussed above, in various embodiments, a diagnosis of gestational diabetes may be based on characteristic similarities or differences (e.g., expression signatures) between a reference sample and a test sample. For example, in various embodiments, if the proteomic profile is presented in the form of a mass spectrum, the expression signature may be a peak or a combination of peaks that differ, qualitatively or quantitatively, from the mass spectrum of a corresponding normal sample. Thus, the appearance of a new peak or a combination of new peaks in the mass spectrum, or any statistically significant change in the amplitude or shape of an existing peak or combination of existing peaks, or the disappearance of an existing peak in the mass spectrum may be considered an expression signature.

Statistical methods for comparing proteomic profiles are well known in the art. For example, in various embodiments employing a mass spectrum, a proteomic profile may be defined by the peak amplitude values at key mass/charge (M/Z) positions along the horizontal axis of the spectrum. Accordingly, in various embodiments, a characteristic proteomic profile may, for example, be characterized by the pattern formed by the combination of spectral amplitudes at given M/Z vales. In various embodiments, the presence or absence of a characteristic expression signature, or the substantial identity of two profiles, may be determined by matching the proteomic profile of a test sample with the proteomic profile of a reference sample with an appropriate algorithm.

Other embodiments may utilize protein arrays to monitor protein expression levels, enabling high-throughput analysis. Protein arrays are known to those of skill in the art, and generally are formed by immobilizing proteins, such as antibodies specific for proteins of interest, on a solid surface, such as glass, silicon, nitrocellulose, or PVDF using any of a variety of covalent and non-covalent attachment chemistries well known in the art. The arrays may be probed with fluorescently labeled proteins from two different sources, such as normal and test samples, and fluorescence intensity may reflect the expression level of a target protein.

Various embodiments also may use any of various immunoassay formats for quantification of protein expression levels. In general, immunoassays may be homogeneous or heterogeneous. For instance, in various embodiments, an enzyme-linked immunosorbant assay (ELISA) may be used to quantify protein expression. In one example, in a "sandwich" assay, a solid surface may be coated with a solid phase antibody, and the test sample may be allowed to react with the bound antibody. Any unbound antigen (e.g., protein of interest) may then be washed away, and a known amount of enzyme-labeled antibody may then be reacted. The label may then be quantified as a direct measurement of the amount of protein of interest present in the sample.

In some embodiments, ELISA may also be used as a competitive assay. For example, in a competitive assay, the test sample containing the protein of interest may be mixed with a precise amount of enzyme-labeled protein of interest, and both may compete for binding to an antibody attached to a solid surface. In various embodiments, excess free enzyme-labeled protein may be washed off before the substrate for the enzyme is added, and the color intensity resulting from the enzyme-substrate interaction may be used as a measure of the amount of protein of interest in the test sample.

Various other embodiments may quantify the proteins of interest using an Enzyme Multiplied Immunoassay Technique (EMIT), which may include a test sample, enzyme-labeled molecules of the proteins of interest, antibodies specific to the proteins of interest, and a specific enzyme chromogenic substrate. In various embodiments, an excess of the specific antibodies may be added to the test sample, and the proteins of interest may then bind to the antibodies. In various embodiments, a measured amount of the corresponding enzyme-labeled proteins may then be added to the mixture, and antibody binding sites not occupied by proteins of interest from the test sample may be occupied with molecules of the enzyme-labeled protein. As a result, in various embodiments, enzyme activity may be reduced because only free enzyme-labeled protein can act on the substrate, and the amount of converted substrate may reflect the amount of free enzyme left in the mixture. In various embodiments, a high concentration of the protein of interest in the sample may result in higher absorbance readings.

Various other embodiments include immunoassay kits for the quantification of the proteins of interest in a test sample. In various embodiments, these kits may include, in separate containers, monoclonal antibodies having binding specificity for each of the proteins of interest, and, optionally, anti-antibody immunoglobulins, particularly labeled anti-antibody immunoglobulins.

Also disclosed herein are capture devices and sample collection kits for use in the disclosed methods. In some embodiments, the disclosed methods may be carried out using a sample capture device, such as a lateral flow device (for example a lateral flow test strip) that may allow quantification of two or more proteins of interest. Lateral flow devices are available in numerous different configurations, but in one example, a test strip may include a flow path from an upstream sample application area to a test site, such as from a sample application area through a mobilization zone to a capture zone. In various embodiments, the mobilization zone may contain a mobilizable marker that may interact with the protein of interest, and the capture zone may contain a reagent that binds the protein of interest for detection and/or quantification. In other embodiments, exemplary sample collection kits may include an absorbent medium, such as filter paper, that may include indicia for the placement of the test sample on the medium. Such kits also may include a lancing device for obtaining a blood sample from a subject, and optionally, a mailer for sending the test sample to a physician or laboratory for analysis. Such sample collection kits may be used, for example, during standard prenatal exams, such as the twelve, sixteen, twenty, or twenty-four-week visit, and/or sample collection may be performed when blood is obtained for other standard prenatal tests.

The following Examples are provided for illustration purposes, and are not to be construed as limiting in any way.

EXAMPLES

Example 1

Subject Selection

A total of 1463 consecutive women within the second and third trimesters of pregnancy underwent a 75-gram OGTT followed by a 2-hour plasma glucose determination. GDM was diagnosed as a 2-hour plasma glucose >7.8 mmol/L, consistent with WHO criteria. All remaining women were categorized as non-diabetic.

Fourteen non-diabetic and 15 GDM participants were randomly selected from the described population. Clinical characteristics of participants are described in Table 1.

TABLE 1

Participant characteristics by GDM status

| Participant Characteristic Mean (SD) | Study Group (n) | | p-value[1] |
|---|---|---|---|
| | Non-diabetic (14) | Gestational Diabetes (15) | |
| Age (years) | 24.2 (3.7) | 24.6 (3.5) | 0.78 |
| Pre-pregnancy Body Mass Index (kg/m²) | 19.6 (3.4) | 20.9 (3.2) | 0.32 |

TABLE 1-continued

Participant characteristics by GDM status

| Participant Characteristic Mean (SD) | Study Group (n) | | p-value[1] |
|---|---|---|---|
| | Non-diabetic (14) | Gestational Diabetes (15) | |
| Percent weight change (%) | 15.2 (4.9) | 14.2 (3.7) | 0.54 |
| Blood Pressure (mmHg) | | | |
| Systolic | 106 (11) | 110 (11) | 0.38 |
| Diastolic | 71 (6) | 69 (7) | 0.45 |
| Total Cholesterol (mg/dl) | 213 (44) | 190 (28) | 0.11 |
| Low-density lipoprotein (mg/dl) | 120 (41) | 104 (30) | 0.23 |
| Very-low-density lipoprotein (mg/dl) | 42 (10) | 38 (13) | 0.4 |
| High-density lipoprotein (mg/dl) | 51 (3) | 49 (4) | 0.11 |
| Median (IQR) | | | |
| Triglycerides (mg/dl) | 222 (178, 238) | 189 (133, 227) | 0.36 |
| Fasting plasma glucose (mg/dl) | 80 (77, 85) | 84 (79, 90) | 0.2 |
| Glycated Hemoglobin (%) | 5.2 (5.0, 5.4) | 5.4 (5.1, 5.8) | 0.23 |
| C-peptide (ng/ml) | 0.9 (0.6, 1.2) | 0.7 (0.4, 1.1) | 0.25 |

Example 2

Proteomic Profiles

Serum samples were analyzed to obtain measures of sex-hormone binding globulin (SHBG), adiponectin, human chorionic gonadotropin (hCG), placental lactogen, C-reactive protein (CRP), pregnancy specific glycoprotein-1 (PSG-1), and fibronectin, as well as specific glycosylated forms of fibronectin and PSG-1 (Table 2). Two-dimensional differential in-gel electrophoresis (2D-DIGE) and immunoassays (ELISA) were performed.

TABLE 2

Differences in serum analyte levels between normal and gestational diabetic pregnant women

| Protein Concentration Median (IQR) | Study Group | | p-value[1] |
|---|---|---|---|
| | Non-diabetic (14) | Gestational Diabetes (15) | |
| C-Reactive Protein (mg/L) | 2.1 (1.0, 4.0) | 5.7 (2.2, 9.0) | 0.05 |
| SHBG (mg/L) | 276 (252, 304) | 240 (173, 278) | 0.12 |
| Adiponectin (mg/mL) | 4.1 (3.3, 5.0) | 3.4 (2.3, 5.2) | 0.28 |
| hCG/Placental Lactogen Ratio | 1.6 (1.0, 2.3) | 3.2 (1.6, 4.3) | 0.03 |
| PSG-1 (AU) | 1.16 (0.96, 1.52) | 1.21 (0.80, 1.40) | 0.95 |
| Fibronectin (mg/L) | 96.0 (78.8, 151.9) | 151.5 (55.4, 238.6) | 0.33 |
| Protein Glycosylation | | | |
| PSG-AAL (AU/mL) | 52.5 (46.7, 71.0) | 85.7 (69.9, 99.5) | 0.004 |
| Fibronectin-SNA (AU/mL) | 51.0 (45.8, 55.1) | 67.0 (53.5, 84.0) | 0.006 |

Differential glycosylation of fibronectin and PSG-1 was determined by direct lectin binding immunoassays. T-tests were used for analysis of normally distributed continuous variables and the Wilcoxon nonparametric equivalent for variables with skewed distribution. Chisquare and Fisher's Exact tests were used for categorical variables. Parametric and Wilcoxon nonparametric t-tests were used to test differences across groups for variables with normal and skewed distributions, respectively. Ratios of proteins were computed and tested across study groups using Wilcoxon nonparametric t-tests.

Receiver Operating Characteristic (ROC) curves generated from predicted probabilities from logistic regression modeling were used to evaluate the classification ability of individual and multiple analyte combinations. The area under the ROC curve (AUROC) was computed from simple logistic regression to describe the classification ability of each protein, ratio, and glycosylated protein individually. Based on the AUROC results, individual proteins, ratios, and glycosylated protein were added sequentially to build a multi-analyte model for improved classification performance. All statistical analyses were performed using SAS software version 9.22 (SAS Institute Inc., Cary, N.C.).

Example 3

Identification of Expression Signature Characteristic of Gestational Diabetes

FIG. 1 illustrates a 2D-DIGE comparison of the total glycoprotein fraction of pooled control and GDM maternal serum, in which protein spots that were differentially abundant in control vs. GDM samples appear as green or red spots, while proteins present at similar levels appear as yellow, in accordance with various embodiments. The arrows point to individual protein spots that correspond to differentially abundant putative biomarkers.

Two specific maternal serum glycoproteins were selected, fibronectin and pregnancy specific glycoprotein (PSG-1), for assessment of potential changes in glycosylation status. Lectin reactivity profiling revealed that fibronectin glycosylation associated with Sambucus nigra lectin (SNA) binding and PSG-1 glycosylation associated with Aleuria aurantia lectin (AAL) binding were significantly elevated in GDM maternal serum vs. control serum. Therefore, these two protein-lectin pairs, fibronectin-SNA and PSG-AAL, were selected for inclusion in a multi-analyte panel with additional biomarkers previously demonstrated to exhibit differential abundance in GDM, including adiponectin, sex hormone binding globulin (SHBG), and C-reactive protein (CRP), as well as the ratio of human chorionic gonadotropin (hCG) to placental lactogen. These analytes were evaluated singly and in combination in a set of control and GDM maternal serum samples from the cohort described in Table 1.

The mean participant age and pre-pregnancy BMI were 24.4+3.5 years and 20.3+3.3 kg/m2, respectively. Glycated hemoglobin measures did not differ between non-diabetic and GDM participants [5.2%(IQR: 5.0-5.4%) and 5.4%(IRQ: 5.1-5.8%), respectively]. Fasting plasma glucose measures were also similar between groups [80 mg/dl (IQR: 77-85 mg/dl) and 84 mg/dl (IQR: 79-90 mg/dl); p=0.20]. In addition, there was no statistically significant difference observed between study groups with regard to any other clinical parameter that was measured.

As shown in Table 2, the levels of PSG-AAL, fibronectin-SNA and the hCG/placental lactogen ratio were significantly elevated in the GDM group (p=0.004, p=0.006 and p=0.03, respectively). The difference in maternal serum CRP levels demonstrated borderline significance (p=0.05), with a median concentration of 2.1 mg/L in non-diabetics and 5.7 mg/L in GDM participants. Thus, combining these proteins in a ratio improves discrimination ability.

Figure 2:
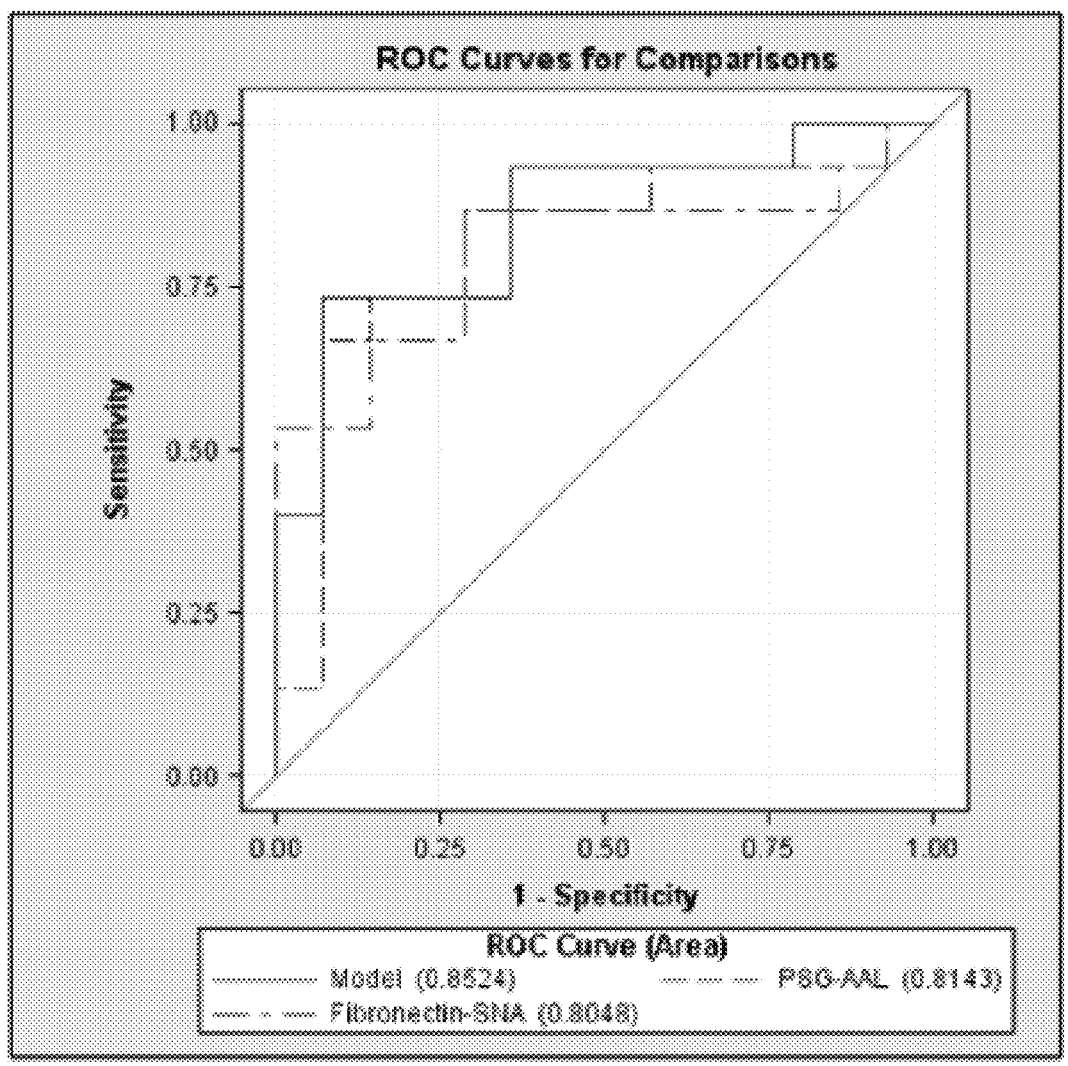
FIG. 2 illustrates receiver operating characteristic (ROC) curves that demonstrate the ability of fibronectin and pregnancy-specific glycoprotein (PSG) glycosylation to distinguish samples from pregnant women with and without gestational diabetes, in accordance with various embodiments.
Figure 3:
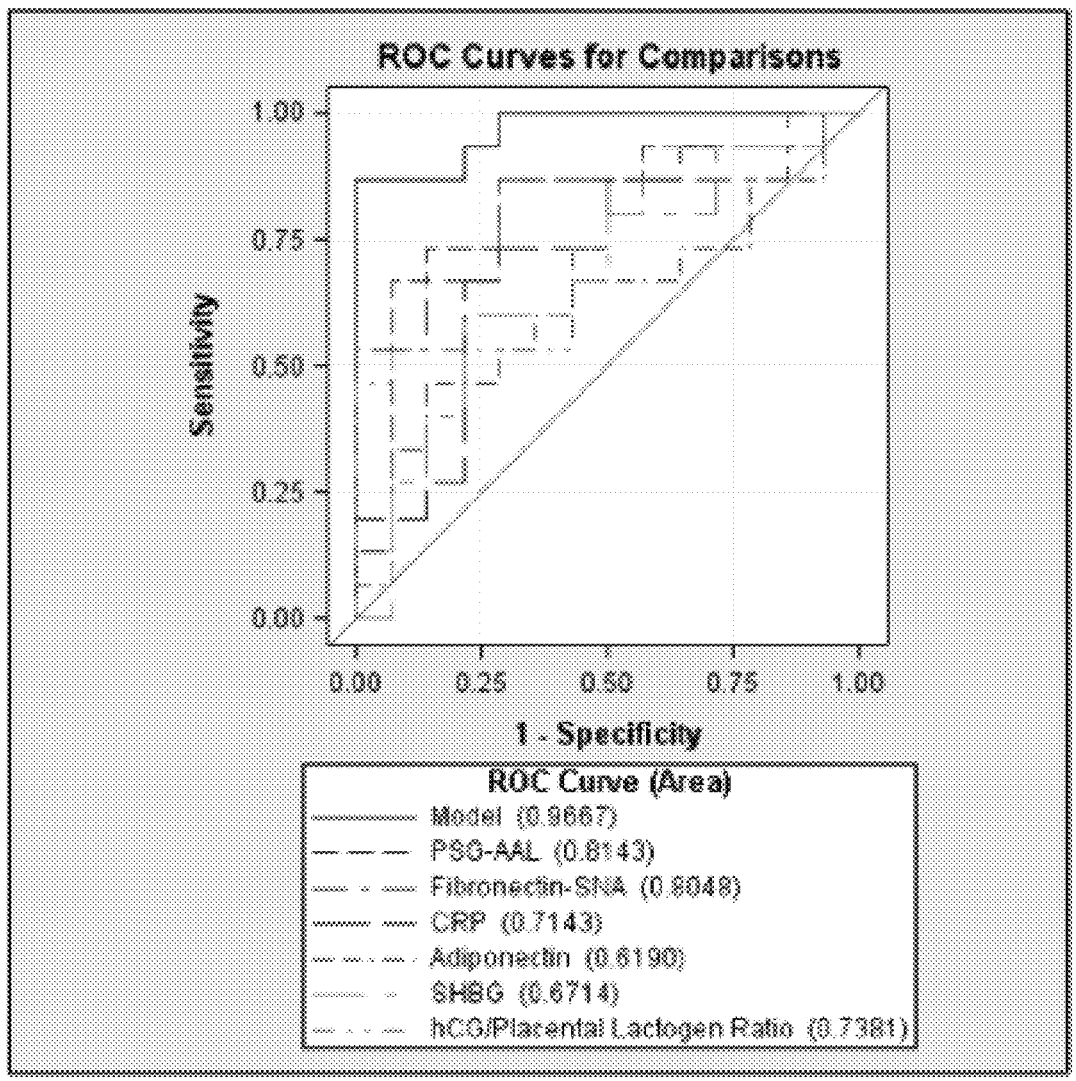
FIG. 3 illustrates ROC curves that demonstrate the classification performance of each protein and protein glycosylation pattern as individual analytes and as a multi-analyte model, in accordance with various embodiments

FIG. 2 illustrates receiver operating characteristic (ROC) curves that demonstrate the ability of fibronectin and pregnancy-specific glycoprotein (PSG) glycosylation to distinguish samples from pregnant women with and without gestational diabetes, in accordance with various embodiments. FIG. 3 illustrates ROC curves that demonstrate the classification performance of each protein and protein glycosylation pattern as individual analytes and as a multi-analyte model; in accordance with various embodiments. While the ability to detect GDM using expression of the two glycosylated proteins PSG-AAL and fibronectin-SNA alone is good (AUROC: 0.85; FIG. 2), their use in conjunction with the other analytes described in Table 2 within a multi-analyte model (FIG. 3) demonstrated clearly superior performance (AUROC: 0.97). Specifically, the combination of fibronectin-SNA and PSG-AAL alone had a detection rate of 74% at a false positive rate of 6% (FIG. 2), while the multi-analyte model had a marked increase in the detection rate (87%) at a false positive rate<1% (FIG. 3).

Thus, a multi-analyte test profile comprised of individual proteins, their ratios, and specific protein glycosylation patterns in maternal serum can identify GDM patients independently classified by OGTT. These analytes are all amenable to analysis in dried blood spots, which enables the use of a minimally invasive, convenient, and cost-efficient screening test for GDM that may be particularly useful for evaluation of underserved populations that suffer significant disparities in diabetes care.

Example 4

Materials and Methods for First-Trimester Serum Panel for Prediction/Detection of GDM Plasma glucose was determined by the hexokinase method using a Konelab 60i Clinical Chemistry Analyzer (Thermo Electron Co, Finland).

Sources (catalog number) and working dilutions of primary antibodies used in ELISAs were as follows: SHBG MAb (31401) from Abcam at 1:250; placental lactogen MAb (L1022-03G) from US Biologicals at 1:250; hCG MAb (MAB605) from Millipore at 1:250; fibronectin MAb (MAB1918) at 1:1000, CRP polyclonal Ab (842676) at 1:180, adiponectin MAb (840965) at 1:180, and PAPPA-2 MAb (MAB1668) at 1:500 from R&D systems; and AFP polyclonal Ab (A0008) at 1:1000 and PAPPA-1 polyclonal Ab (A0230) at 1:1000 from Dako.

Levels of protein analytes were determined by sandwich ELISA. Primary coating antibodies were resuspended in carbonate buffer (pH 9.6) and 100 µl added to each well of a 96-well Reactibind plate (Pierce) and incubated at 4° C. overnight. Plates were blocked with 3% BSA in PBS (pH 7.2). Following sample addition and incubation for 45 minutes at room temperature, plates were washed with PBST using a Biotek plate washer, and then incubated with detection antibodies for 45 minutes at room temperature. Plates were again washed with PBST and then incubated with streptavidin-HRP (50 ng/ml in PBS; Pierce) for 45 minutes at room temperature, and then washed with PBST. TMB substrate (Neogen) was added and, following the development of the signal, quenched by the addition of 2N $H_2SO_4$. The plate was read using an EPOCH plate reader (Biotek) at 490 nm, and data was processed using Gen5 software version 1.10.8. Data was then analyzed as described below in Example 6. A reference sample was run on each plate. For the serial measures assay run, samples from all three trimesters for each participant were included on the same plate. The inter-assay coefficient of variation (CV) for all assays was <10%.

For assay of Fibronectin-SNA, the Fibronectin MAb was used to coat Reactibind plates which were then blocked as described above. The blocking solution was then removed and 200 µl/well of oxidation buffer (100 mM sodium periodate, 50 mM citric acid, pH 4.0) was added and the plate incubated for 14 minutes. The oxidation solution was then removed and the plate washed with PBST before sample addition. Samples were applied at a 1:800 dilution, after which the plate was washed with PBST. Biotin-conjugated SNA (Vector Labs) was then added to a final concentration of 0.5 ng/µl in PBS. After washing the plate with PBST, the plate was incubated with Streptavidin-HRP and processed as above. The inter-assay CV for FN-SNA was 17%.

Example 5

Subject Population for First-Trimester Serum Panel for Prediction/Detection of GDM The Finnish Maternity Cohort is a prospective study derived from the serum bank at the National Institute for Health and Welfare (Finland). Participants were recruited from maternity clinics in the area of Oulu University Hospital (Oulu, Finland) and Kuopio University Hospital (Kuopio, Finland) between 2004 and 2010. Serum samples were drawn during regular pre-natal exams, and clinical data was obtained from the Birth Register, a computerized database containing information on maternal characteristics and pregnancy outcome.

The present analysis employed a case-control design, in which a total of 90 cases and 92 controls were randomly selected from the described population. Participants needed a sufficient quantity of 1st-trimester serum collected between 5 and 13 weeks gestation for inclusion. Eligible GDM cases included any woman who developed GDM during pregnancy, identified by a standard 75-g OGTT followed by 2-hour plasma glucose determination. GDM was diagnosed as a 2-hour plasma glucose>140 mg/dl (7.8 mmol/L), consistent with World Health Organization criteria. Non-diabetic controls were selected from the same population as cases, but did not develop GDM during pregnancy. Maternal characteristics and pregnancy outcome information were extracted from the same database for both groups. Clinical data was unable to be extracted from the birth register for 13 non-diabetic Controls. There was no material difference in serum analyte concentration between non-diabetic controls with and without clinical data.

Figure 4:
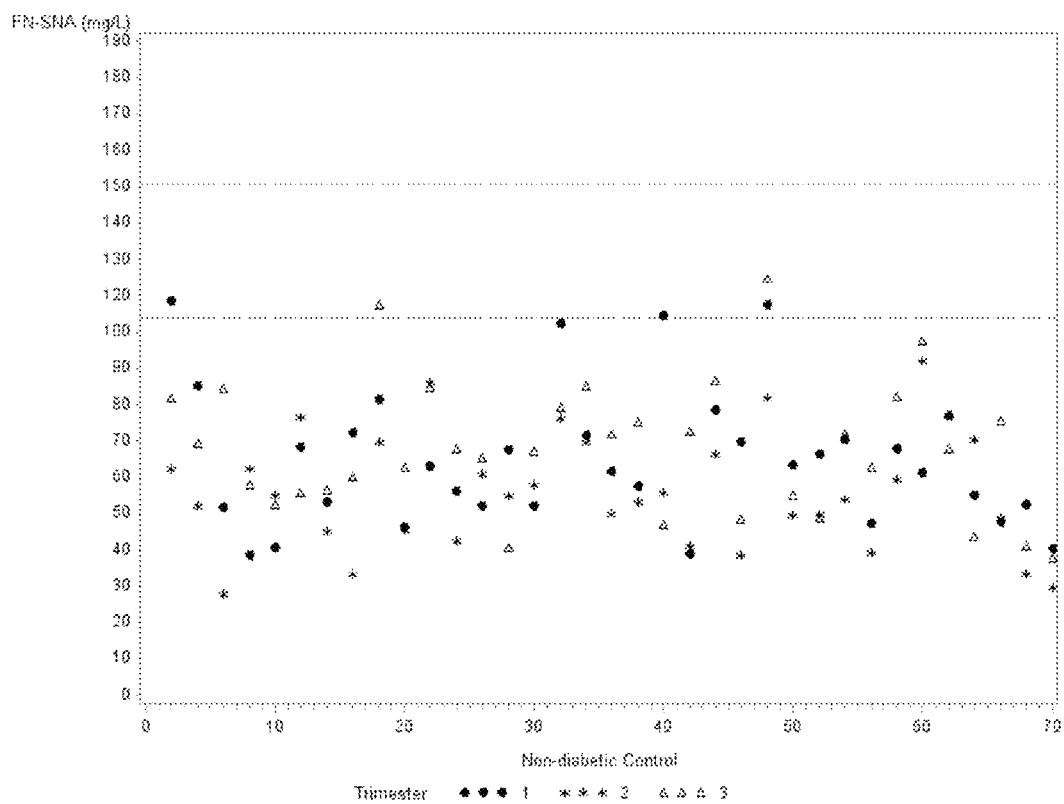
FIG. 4 illustrates serial measures of fibronectin-SNA across trimesters in 35 non-diabetic controls, in which the lines represent the 25th and 75th percentile of the GDM study group, in accordance with various embodiments.

In addition to 1st-trimester serum, 35 non-diabetic controls had serum samples drawn during the 2nd and 3rd trimester. These participants were included in a serial measures analysis to evaluate the change in FN-SNA concentration across trimester (FIG. 4).

Example 6

Statistical Analysis for First-Trimester Serum Panel for Prediction/Detection of GDM A thorough descriptive analysis was performed for each maternal characteristic and serum analyte measure. Distributions of maternal characteristics according to study group were compared using 2-sided independent t-tests for continuous variables and Chi-square and Fisher's exact tests for categorical variables. The Wilcoxon nonparametric t-test was used for comparisons across groups for continuous variables with skewed distributions. In participants with serial measures of fibronectin-SNA, least square means by trimester were computed and compared using mixed models. The serial measures of fibronectin-SNA were plotted and repeatability was quantified using a two-way, mixed effect intraclass correlation coefficient.

The independent association between each serum analyte and subsequent development of GDM was evaluated using univariate and multivariate log-binomial regression. Risk ratios (RR) and 95% confidence intervals (CI) may be derived from this method using a poisson distribution with robust variance estimation. Serum analytes were categorized into tertiles and evaluated in univariate and multivariate models. The first model was adjusted for baseline maternal factors including maternal age, nulliparity, and gestational age at sample collection. The second model included all baseline maternal factors in addition to each serum analyte significantly associated with GDM status (p<0.05). Fibronectin-SNA, adiponectin, hs-CRP, and placental lactogen were included in multivariate log-binomial regression analyses (FIG. 4).

To evaluate the clinical utility of these serum analytes as individual biomarkers and as a potential first-trimester panel for prediction of GDM, Receiver Operating Characteristic (ROC) Curves were generated from predicted probabilities from logistic regression modeling. The area under the ROC curve (AUROC) and 95% confidence interval (CI) was computed from simple logistic regression to describe the GDM classification ability of each serum analyte individually. A multi-analyte GDM screening panel comprised of fibronectin-SNA, adiponectin, hs-CRP, and placental lactogen was assessed to determine the discrimination of the multi-analyte model compared to single analytes. A backward-selection process was utilized to evaluate the contribution of each analyte to the multi-analyte panel and determine if serum analytes were additive. Additional ROC curves were generated to determine if the classification performance of the multi-analyte panel varied by maternal parity or time to GDM diagnosis.

Two-sided p-values are reported, and a value of less than 0.05 was considered statistically significant. All statistical analyses were performed using SAS software version 9.3 (SAS Institute Inc., Cary, N.C.).

Example 7

2D-DIGE for First-Trimester Serum Panel for Prediction/Detection of GDM

GDM was associated with changes in the GDM maternal serum glycoproteome as assessed by 2D-DIGE. This is illustrated in FIG. 1, which shows a 2D-DIGE comparison of the total glycoprotein fraction of pooled control and GDM maternal serum, in which protein spots that were differentially abundant in control vs. GDM samples appear as green or red spots, while proteins present at similar levels appear as yellow. The arrows point to individual protein spots that correspond to differentially abundant candidate biomarkers.

In subsequent analyses, fibronectin was selected for assessment of potential changes in glycosylation status. Lectin reactivity profiling revealed that fibronectin glycosylation associated with Sambucus nigra lectin (SNA) binding (FN-SNA) was significantly elevated in 1st-trimester GDM maternal serum vs. control serum. Therefore, FN-SNA was included in a multi-analyte panel with additional biomarkers previously demonstrated to exhibit differential abundance in GDM, including adiponectin, sex hormone binding globulin (SHBG), and C-reactive protein (CRP), as well as the ratio of human chorionic gonadotropin (hCG) to placental lactogen. These analytes were evaluated singly and in combination in a set of control and GDM maternal serum samples from the cohort described in Table 3, below.

First-trimester concentrations of FN-SNA, adiponectin, hs-CRP, and placental lactogen were significantly associated with GDM status (p<0.001; Table 3). In particular, FN-SNA demonstrated markedly higher concentrations in GDM compared to non-diabetic controls, with minimal overlap in group distributions [mean (95% CI): 132 (124, 139) mg/L vs. 80 (72, 87) mg/L, respectively; p<0.0001].

The risk of subsequent development of GDM increased with increasing tertile for FN-SNA, hs-CRP, and placental lactogen (Table 4, below). Adiponectin demonstrated significantly greater risk of GDM if 1st-trimester concentrations were below the first tertile (<2.2 µg/ml), but no significant difference in risk ratios between the 2nd and 3rd tertiles (p=0.15). Multivariate analyses demonstrated marked attenu-

TABLE 3

First-trimester serum protein and protein glycosylation concentration by gestational diabetes status.

| Maternal Characteristic Mean (SD) | Study Group (n) | | p-value[1] |
|---|---|---|---|
| | Non-diabetic Controls (92) | Gestational Diabetes (90) | |
| Maternal age (years) | 26.2 (4.0) | 31.3 (6.0) | <0.0001 |
| Gestational age at sample collection (weeks) | 9.7 (1.4) | 10.1 (0.8) | 0.009 |
| Gestational age at delivery (weeks)[2] | 40.2 (1.1) | 39.7 (1.6) | 0.03 |
| Infant birthweight (g)[2] | 3563 (401) | 3644 (512) | 0.26 |
| Number (%) | | | |
| Nulliparity[2] | 62 (82) | 29 (32) | <0.0001 |
| Macrosomia (>4000 g)[2] | 12 (16) | 20 (22) | 0.36 |
| Serum Analyte Concentration Mean (SD) | | | |
| Fibronectin-SNA (mg/L) | 80 (35) | 132 (36) | <0.0001 |
| Adiponectin (µg/ml) | 3.0 (1.2) | 2.5 (0.9) | 0.001 |
| SHBG (nmol/L) | 91 (66) | 84 (46) | 0.43 |
| Median (IQR) | | | |
| C-reactive protein (mg/L) | 0.39 (0.17, 1.24) | 1.17 (0.52, 2.04) | <0.0001 |
| Placental Lactogen (mg/L) | 0.22 (0.05, 0.36) | 0.34 (0.23, 0.63) | <0.0001 |
| hCG (mIU/ml) | 60911 (50655, 72984) | 61542 (48287, 70467) | 0.65 |

[1]Comparisons were made using a 2-sided independent t-test and Wilcoxon 2-sided nonparametric t-test for continuous variables. Chi-square and Fisher's exact tests were used for categorical variables.
[2]Gestational age at delivery, birthweight, and parity data was unavailable for 20, 19, and 16 non-diabetic controls, respectively.

Example 8

First-Trimester Case-Control Analysis

The mean gestational age at sample collection was 9.9+1.2 weeks (range: 5.7-13.1) and was not markedly different between GDM and non-diabetic control participants (10.2+0.8 weeks and 9.7+1.4 weeks, respectively). GDM participants were older (31.4+5.9 years vs. 26.2+4.0 years; p<0.0001) and less likely to be nulliparous (34% vs. 82%; p<0.0001) than non-diabetic controls (Table 3). In GDM participants, the mean gestational age at diagnosis was 22.2+6.2 weeks with an average of 12.6+6.0 weeks between the 1st-trimester serum draw and GDM diagnosis.

ation of risk ratios for all serum analytes upon adjustment for maternal age, nulliparity, and gestational age at sample collection. Despite this, FN-SNA had a strong independent association with GDM after adjustment for these maternal factors. In addition, when FN-SNA concentrations<80 mg/L were used as the referent group, risk ratios increased between the 2nd and 3rd tertile [RR (95% CI): 4.81 (1.85, 12.49) and 7.62 (2.97, 19.58), respectively]. The difference between the 2nd and 3rd tertiles was statistically significant (p<0.0001). Upon addition of all serum analytes to the maternal factors model, there was minimal change in FN-SNA risk ratios. In this fully adjusted model, only FN-SNA and placental lactogen demonstrated significant independent associations with development of GDM in this population.

TABLE 4

Risk of subsequent gestational diabetes across tertiles of first-trimester serum protein and protein glycosylation concentration.

| | Univariate Analysis | | Multivariate Analysis | | | |
|---|---|---|---|---|---|---|
| | | | Maternal factors[1] | | Maternal factors + serum analytes | |
| | RR (95% CI)[2] | p-value | RR (95% CI)[2] | p-value | RR (95% CI)[2] | p-value |
| Fibronectin-SNA (mg/L) | | | | | | |
| >122 | 13.77 (5.33, 35.60) | <0.0001 | 7.62 (2.97, 19.58) | <0.0001 | 7.22 (2.86, 18.21) | <0.0001 |
| 80-122 | 7.38 (2.77, 19.67) | <0.0001 | 4.81 (1.85, 12.49) | 0.001 | 4.69 (1.85, 11.90) | 0.001 |
| <80 | 1.00 | | 1.00 | | 1.00 | |
| C-reactive protein (mg/L) | | | | | | |
| >1.30 | 2.24 (1.47, 3.42) | 0.0002 | 1.41 (0.96, 2.09) | 0.08 | 1.03 (0.76, 1.40) | 0.85 |
| 0.34-1.30 | 1.69 (1.07, 2.68) | 0.02 | 1.11 (0.73, 1.67) | 0.62 | 0.99 (0.72, 1.35) | 0.94 |
| <0.34 | 1.00 | | 1.00 | | 1.00 | |
| Placental lactogen (ng/ml) | | | | | | |
| >0.37 | 2.31 (1.49, 3.60) | 0.0002 | 1.51 (1.00, 2.30) | 0.05 | 1.43 (1.05, 1.94) | 0.02 |
| 0.20-0.37 | 1.91 (1.20, 3.04) | 0.006 | 1.63 (1.10, 2.39) | 0.01 | 1.46 (1.08, 1.98) | 0.01 |
| <0.20 | 1.00 | | 1.00 | | 1.00 | |
| Adiponectin (µg/ml) | | | | | | |
| >3.1 | 1.00 | | 1.00 | | 1.00 | |
| 2.2-3.1 | 1.36 (0.90, 2.08) | 0.15 | 1.18 (0.84, 1.68) | 0.34 | 1.13 (0.85, 1.51) | 0.41 |
| <2.2 | 1.76 (1.19, 2.58) | 0.004 | 1.33 (0.96, 1.83) | 0.09 | 1.30 (0.99, 1.70) | 0.06 |

Figure 5:
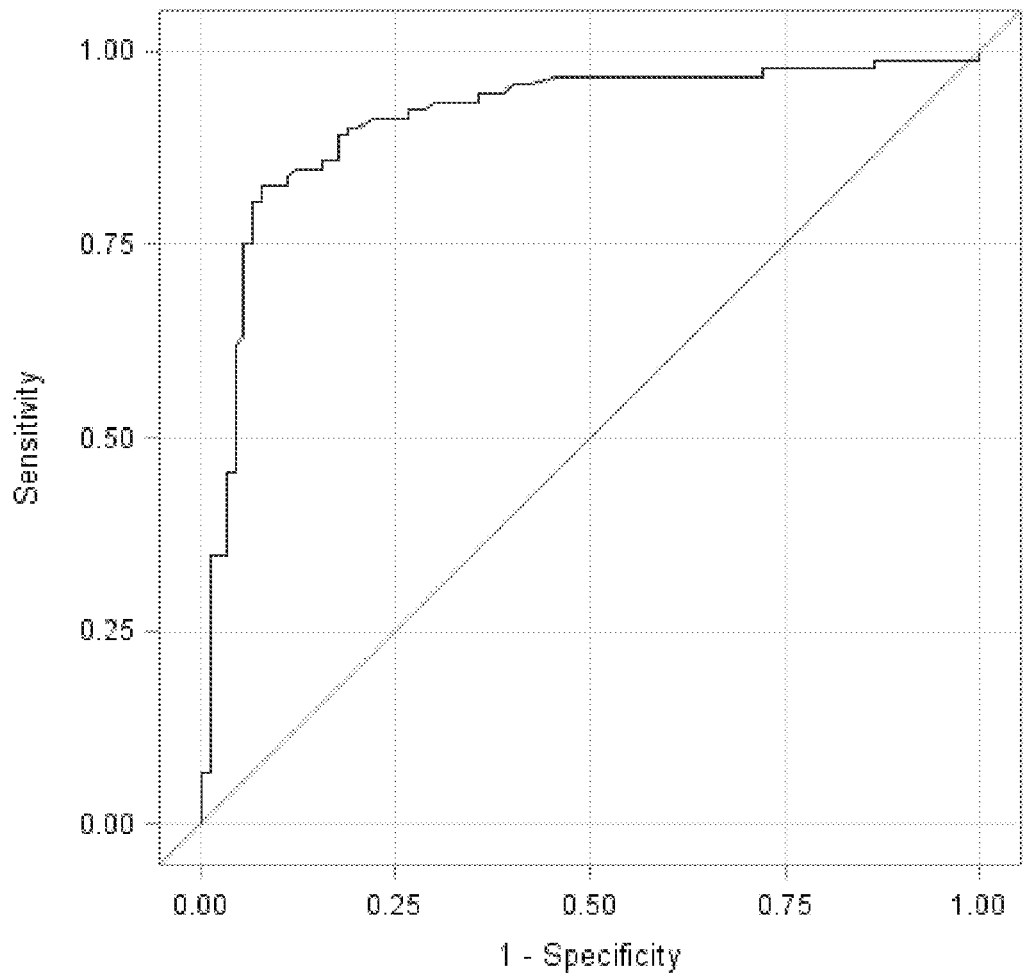
FIG. 5 is a Receiver Operating Characteristic (ROC) curve illustrating the ability of first trimester fibronectin-SNA to predict subsequent development of gestational diabetes, in accordance with various embodiments.

[1]Adjustment for maternal factors includes maternal age, gestation age at sample Since statistically significant associations with a disease or outcome do not always translate into strong diagnostic accuracy, the clinical utility of these tests was quantified using ROC analyses. The ROC curve is a plot of the sensitivity of a diagnostic test across all possible false-positive fractions (1-specificity; FIG. 5). The AUROC is a statistic that can be used to compare the classification performance of diagnostic tests. An AUROC of 1.00 reflects perfect discrimination between the groups under study while an AUROC of 0.50 indicates no discrimination. As illustrated in Table 5, below, FN-SNA alone had an AUROC of 0.91 (95% CI: 0.87, 0.96). This translates to detection rate of 82% of GDM cases from 1st-trimester serum screening at a false-positive rate of 10%. Despite strong univariate associations with GDM status, hs-CRP, adiponectin, and placental lactogen demonstrated only marginal classification performance. To test whether combining these tests into a multi-analyte model improved diagnostic accuracy, the AUROC was computed for FN-SNA, adiponectin, hs-CRP, and placental lactogen. The multi-analyte model yielded an AUROC of 0.91 (95% CI: 0.88, 0.96), which was not significantly different than the performance of FN-SNA alone (p=0.48).

TABLE 5

Classification performance of each protein and protein glycosylation as a first-trimester individual test and as a multi-analyte panel.

| | | Sensitivity at fixed false-positive fractions | | | |
|---|---|---|---|---|---|
| Screening Test | AUROC (95% CI) | 5% | 10% | 15% | 20% |
| Fibronectin-SNA | 0.91 (0.87, 0.96) | 64 | 82 | 85 | 94 |
| C-reactive protein | 0.68 (0.60, 0.76) | 6 | 18 | 28 | 46 |
| Placental lactogen | 0.67 (0.59, 0.75) | 7 | 16 | 27 | 42 |
| Adiponectin | 0.63 (0.55, 0.71) | 12 | 30 | 35 | 38 |
| Multi-analyte model Fibronectin-SNA C-reactive protein Adiponectin Placental Lactogen | 0.92 (0.88, 0.96) | 66 | 78 | 85 | 92 |

[1]Area under the Receiver Operating Characteristic Curve (AUROC) and 95% CI were obtained using univariate and multivariate logistic regression modeling.

Stratification by key maternal characteristics was performed to determine if the classification performance was influence by these factors. Upon stratification for nulliparity, no difference was observed in the AUROC of FN-SNA. In addition, the time between 1st-trimester screening and diagnosis of GDM may influence the diagnostic accuracy of the test if FN-SNA can only detect current or imminent GDM. When the analysis was restricted to cases with a GDM diagnosis occurring more than 10 weeks since their 1st-trimester sample collection, the FN-SNA AUROC was similar [AUROC (95% CI): 0.92 (0.87, 0.96)]. Furthermore, no correlation was observed between FN-SNA concentration and time between 1st-trimester sample collection and GDM diagnosis (r=−0.06).

Example 9

Fibronectin-SNA Serial Measures

The intraclass correlation coefficient demonstrated modest FN-SNA repeatability across trimester in non-diabetic controls with repeated serum measures (r=0.44). A significant difference in FN-SNA concentration was observed across the first, second, and third trimesters [mean (95% CI): 66 (59, 72) mg/L, 56 (50, 63) mg/L and 69 (62, 75) mg/L, respectively; p=0.003]. There was no significant difference between the first and third trimester with regard to FN-SNA concentration (p=0.51). Despite change across trimesters, only 4 non-diabetic control participants had FN-SNA concentrations above the 25th percentile of the 1st-trimester GDM population.

These analyses illustrate the utility of a panel comprised of individual protein analytes, analyte ratios, and specific protein glycosylation in maternal serum to efficiently identify GDM patients independently classified by OGTT. The robust performance of FN-SNA alone in both 1st, 2nd, and 3rd trimesters, coupled with its enhanced 1st-trimester performance with the addition of CRP, SHBG, and the hCG/placental lactogen ratio, supports the use of this panel for both early screening and subsequent confirmation/diagnosis of GDM. In fact, the performance of fibronectin-SNA alone in terms of specificity and sensitivity, surpasses that of the 50 g glucose challenge test which has been proposed as a screening precursor to the standard OGTT. These analytes are all amenable to analysis in dried blood spots, which enables the use of a minimally invasive, convenient, and cost-efficient screening test for GDM that is particularly useful for evaluation of underserved populations that suffer significant disparities in diabetes care.

The majority of the components of the multianalyte panel, in addition to fibronectin-SNA itself, are also glycoproteins, and their glycosylation has been reported to be altered in pathological conditions to modulate serum stability or regulate activity. Thus, their utility in identification of GDM further supports the notion that the glycoproteome constitutes an important class of biomarkers that is intimately connected to cellular function and pathophysiology.

Example 10

Serum Markers for Diagnosis of GDM

A total of 1463 consecutive women within the second and third trimester of pregnancy underwent a 75 g oral glucose tolerance test (OGTT) followed by a 2-hour plasma glucose (PG). Gestational diabetes (GDM) was diagnosed as a 2-hour PG>7.8 mmol/L, consistent with WHO criteria. All remaining women were categorized as non-diabetic.

A case-control design was used in which 14 non-diabetic and 15 GDM participants were randomly selected from the described population. Blood samples from the OGTT were used to obtain measures of sex-hormone binding globulin (SHBG), adiponectin, human chorionic gonadotropin (hCG), placental lactogen, C-reactive protein (CRP), PSG-1, and fibronectin as well the glycosylated form of fibronectin and PSG-1.

Differential glycosylation of specific proteins (e.g., fibronectin and PSG-1) was determined by direct lectin binding assay, in which proteins were immunoprecipitated from maternal serum. Maternal serum levels of total fibronectin and PSG-1, adiponectin, CRP, hCG, and placental lactogen were assayed by commercial ELISA kits.

A thorough descriptive analysis was performed for each protein, glycosylated protein and participant characteristic. Parametric and Wilcoxon nonparametric t-tests were used to test differences across study groups for variables with a normal and skewed distribution, respectively. Ratios of proteins were computed and tested across study groups using Wilcoxon nonparametric t-tests.

Receiver Operating Characteristic (ROC) Curves generated from predicted probabilities from logistic regression modeling can be used to evaluate the classification ability of individual and multiple analyte combinations. The area under the ROC curve (AUROC) was computed from simple logistic regression to describe the classification ability of each protein, ratio, and glycosylated protein individually. Based on AUROC results, individual proteins, ratios, and glycosylated protein were added sequentially to build a multi-analyte model for improved classification performance.

All statistical analyses were performed using SAS software version 9.22 (SAS Institute Inc., Cary, N.C.).

Characteristics of the sample population are described in Table 6, below. The mean participant age and pre-pregnancy BMI were 24.4+3.5 years and 20.3+3.3 kg/m2, respectively. Glycated hemoglobin measures did not differ between non-diabetic and GDM participants [5.2%(IQR: 5.0-5.4%) and 5.4%(IRQ: 5.1-5.8%), respectively]. Fasting plasma glucose measures were also similar between groups [80 mg/dl (IQR: 77-85 mg/dl) and 84 mg/dl (IQR: 79-90 mg/dl); p=0.20]. In addition, there was no statistically significant difference observed between study groups with regard to any other clinical parameter that was measured.

TABLE 6

Participant characteristics by gestational diabetes status

| Participant Characteristic Mean (SD) | Study Group (n) | | p-value[1] |
|---|---|---|---|
| | Non-diabetic (14) | Gestational Diabetes (15) | |
| Age (years) | 24.2 (3.7) | 24.6 (3.5) | 0.78 |
| Pre-pregnancy body mass index (kg/m$^2$) | 19.6 (3.4) | 20.9 (3.2) | 0.32 |
| Percent weight change (%) | 15.2 (4.9) | 14.2 (3.7) | 0.54 |
| Blood pressure (mmHg) | | | |
| Systolic | 106 (11) | 110 (11) | 0.38 |
| Diastolic | 71 (6) | 69 (7) | 0.45 |
| Total cholesterol (mg/dl) | 213 (44) | 190 (28) | 0.11 |
| Low-density lipoprotein (mg/dl) | 120 (41) | 104 (30) | 0.23 |
| High-density lipoprotein (mg/dl) | 51 (3) | 49 (4) | 0.11 |
| Median (IQR) | | | |
| Triglycerides (mg/dl) | 222 (178, 238) | 189 (133, 227) | 0.36 |
| Fasting plasma glucose (mg/dl) | 80 (77, 85) | 84 (79, 90) | 0.20 |
| Glycated hemoglobin (%) | 5.2 (5.0, 5.4) | 5.4 (5.1, 5.8) | 0.23 |
| C-peptide (ng/ml) | 0.9 (0.6, 1.2) | 0.7 (0.4, 1.1) | 0.25 |

[1]T-tests for normally distributed continuous variables and the Wilcoxon nonparametric equivalent for variables with a skewed distribution. Chi-square and Fisher's Exact tests were used for categorical variables.

As shown in Table 7, below, the levels of PSG-AAL and fibronectin-SNA were each significantly elevated in the GDM group, as was the hCG/placental lactogen ratio. While hCG and placental lactogen have been reported to exhibit altered levels in GDM maternal serum, their ratio was clearly highly discriminant in this sample set.

TABLE 7

Protein concentration and glycosylation by gestational diabetes status

| Protein Concentration Median (IQR) | Study Group (n) | | p-value[1] |
|---|---|---|---|
| | Non-diabetic (14) | Gestational Diabetes (15) | |
| C-Reactive Protein (mg/L) | 2.1 (1.0, 4.0) | 5.7 (2.2, 9.0) | 0.05 |
| SHBG (nmol/L) | 276 (252, 304) | 240 (173, 278) | 0.12 |
| Adiponectin (µg/mL) | 4.1 (3.3, 5.0) | 3.4 (2.3, 5.2) | 0.28 |
| hCG/Placental Lactogen Ratio | 1.6 (1.0, 2.3) | 3.2 (1.6, 4.3) | 0.03 |
| PSG-1 (AU) | 1.16 (0.96, 1.52) | 1.21 (0.80, 1.40) | 0.95 |
| Fibronectin (mg/L) | 96.0 (78.8, 151.9) | 151.5 (55.4, 238.6) | 0.33 |
| Protein Glycosylation (arbitrary units) | | | |
| PSG-AAL | 52.5 (46.7, 71.0) | 85.7 (69.9, 99.5) | 0.004 |
| Fibronectin-SNA | 51.0 (45.8, 55.1) | 67.0 (53.5, 84.0) | 0.006 |

[1]Wilcoxon nonparametric t-test

Figure 6:
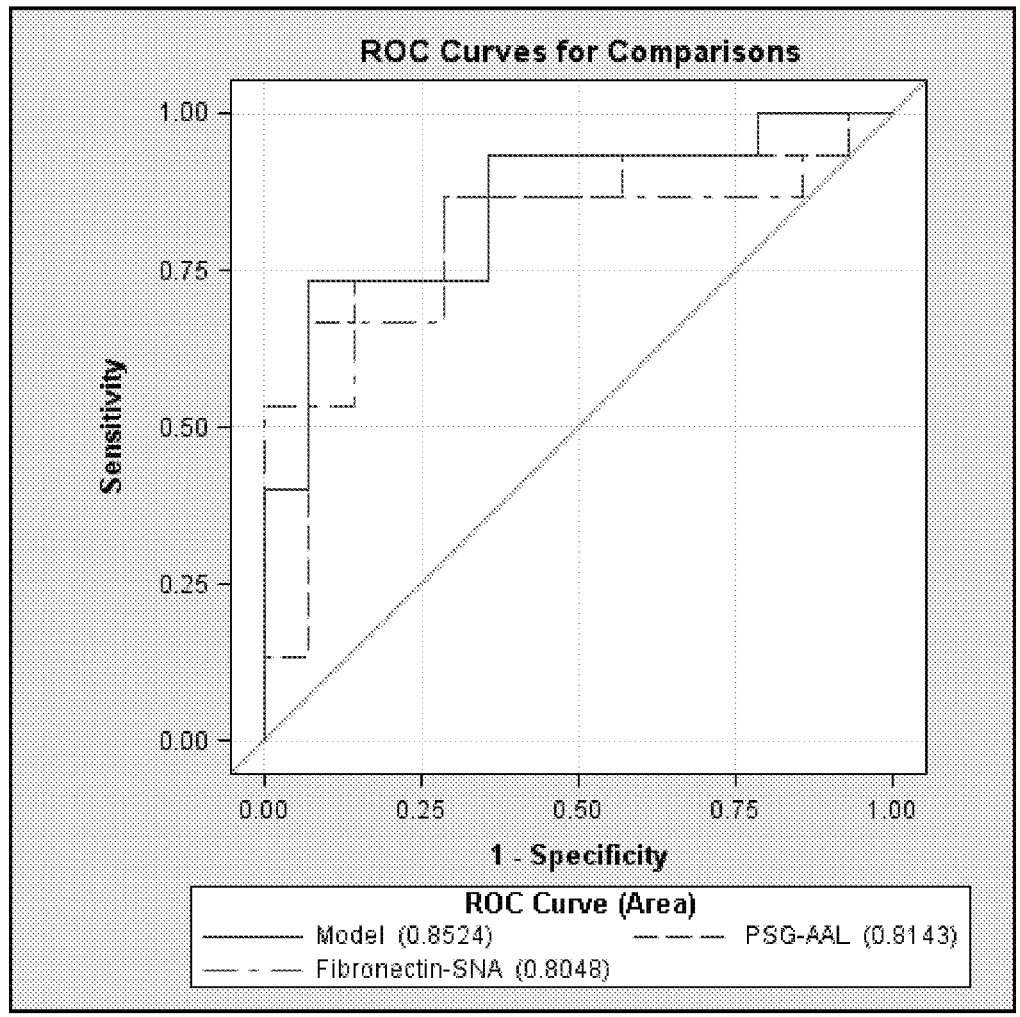
FIG. 6 is a Receiver Operating Characteristic (ROC) Curve, illustrating the ability of fibronectin and PSG glycosylation to distinguish between non-diabetics and gestational diabetics within the second and third trimesters of pregnancy, in accordance with various embodiments.
Figure 7:
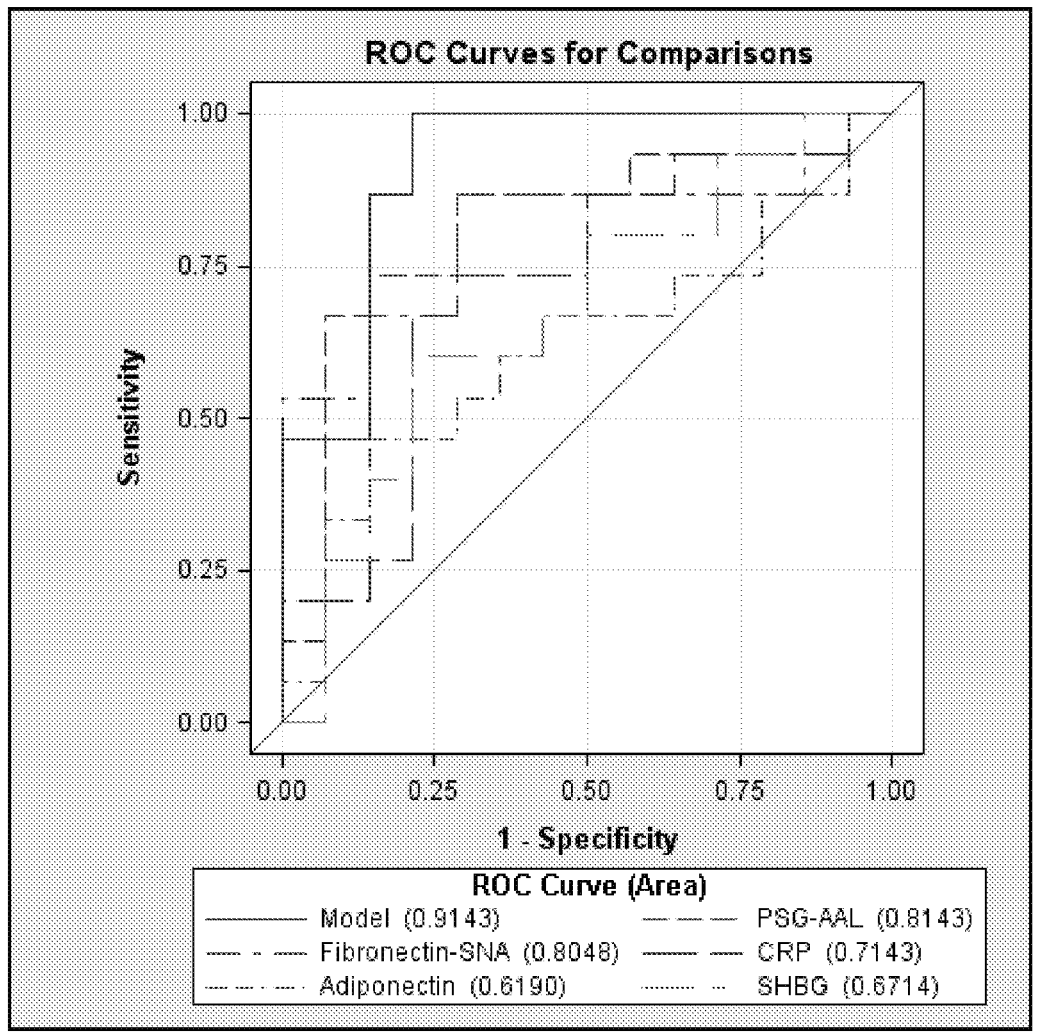
FIG. 7 is a Receiver Operating Characteristic (ROC) Curve, illustrating the classification performance of each protein and protein glycosylation pattern as individual analytes and as a multi-analyte model, in accordance with various embodiments.

Receiver-operator characteristics (ROC) curves utilizing fibronectin-SNA and PSG-AAL as well as the combination are shown in FIG. 6. While the sensitivity and specificity of these two analytes for detecting GDM is good, the additional of the additional analytes in Table 7 in a multi-analyte model (FIG. 7) demonstrated clearly superior performance, even though these analytes themselves were not significantly differentially abundant individually in non-diabetic vs. GDM maternal serum.

Example 11

Fibronectin Lateral Flow Immunoassay (FN LFIA)

Various lateral flow assay methods may be utilized to test for the presence or absence or quantity of an analyte in a biological sample. In one example, a "sandwich" assay method uses an antibody immobilized on a solid support, which forms part of a complex with a labeled antibody, to determine the presence of a target analyte by observing the presence and amount of bound analyte-labeled antibody complex. For the purposes of a lateral flow immunoassay, the label may be an enzyme, colored microspheres, fluorescently-labeled microspheres, or may use other similar detection methods that provide for detection and/or quantification of analyte bound to the test line.

Conventional lateral flow test strips feature a solid support on which the sample receiving area and the target capture zones are supported. The solid support material is one which is capable of supporting the sample receiving area and target capture zones and providing for the capillary flow of sample out from the sample receiving area to the target capture zones when the lateral flow test strip is exposed to an appropriate solvent or buffer which acts as a carrier liquid for the sample. General classes of materials that may be used as support include organic or inorganic polymers, and natural and synthetic polymers. More specific examples of suitable solid supports include, without limitation, glass fiber, cellulose, nylon, crosslinked dextran, various chromatographic papers and nitrocellulose. One particularly useful material is nitrocellulose.

Figure 8A:
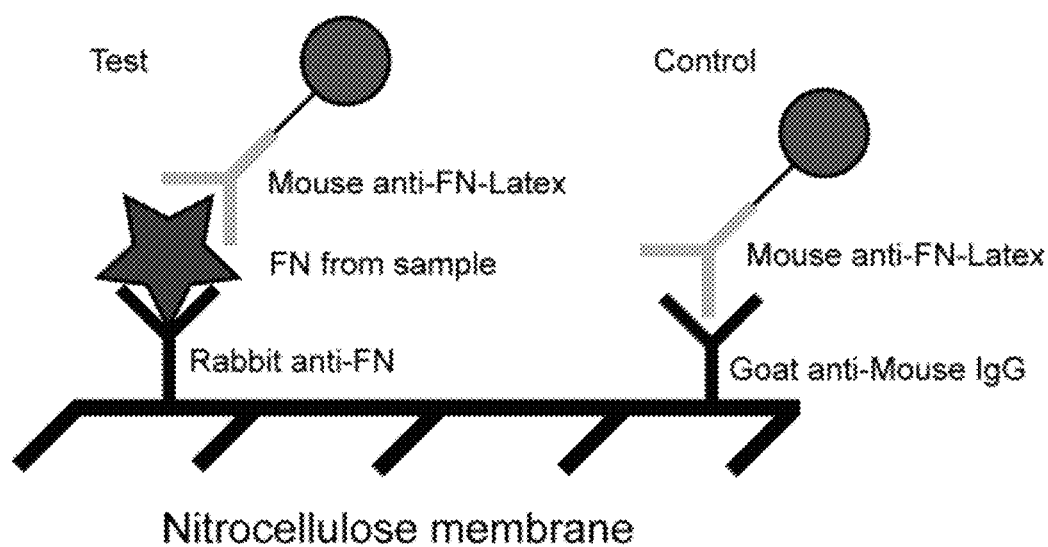
FIGS. 8A and 8B illustrate a schematic diagram showing an example of a lateral flow immunoassay (FIG. 8A) and a lateral flow device (FIG. 8B) that may be used in accordance with various embodiments disclosed herein.
Figure 8B:
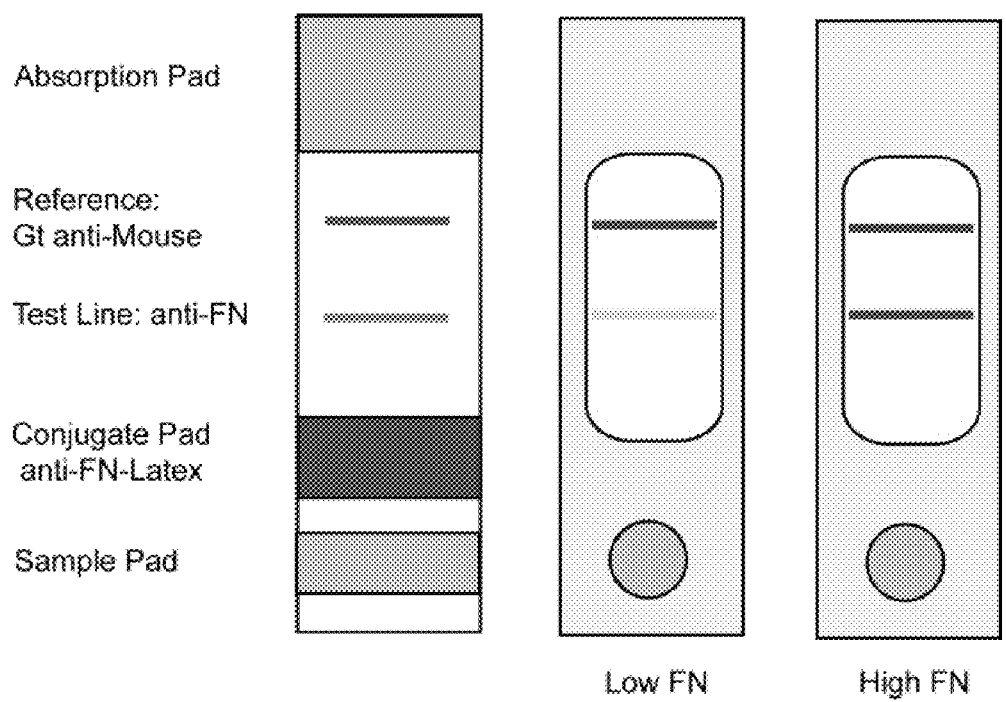

FIGS. 8A and 8B illustrate a schematic diagram showing an example of a lateral flow immunoassay (FIG. 8A) and a lateral flow test device (FIG. 8B) that may be used in accordance with various embodiments disclosed herein. Briefly, 200 µg/mL Rabbit anti-fibronectin was immobilized on the membrane as a test line (0.5 µL/strip) and 300 µg/mL goat anti-mouse IgG was immobilized as the procedural control line (0.5 µL/strip). Mouse anti-fibronectin-conjugated microspheres (10 µL of 150 µg/mL mouse anti-fibronectin, 1 mg/mL solids) were dried onto a conjugate pad that had been treated with a solution containing (per liter): 3.81 g Sodium Borate, 2.0 g Dextran, 5.0 g BSA, 1.0 g Tween-20, and 0.5 g Sodium Azide, pH 8.0, followed by drying for 1 hour at 50° C.

The sample was then diluted 1:500 in HEPES Running Buffer (10 mM HEPES, 0.1 mM $CaCl_2$, 155 mM NaCl, 0.1% $NaN_3$, 0.75% Tween-20, and 0.01% Polyvinyl alcohol). When the sample was applied to the sample pad, capillary flow allowed the fibronectin-containing sample to hydrate and interact with the labeled microspheres, forming fibronectin-labeled microsphere complexes, which further migrated to the test line, where they were captured by the rabbit anti-fibronectin.

Figure 9:
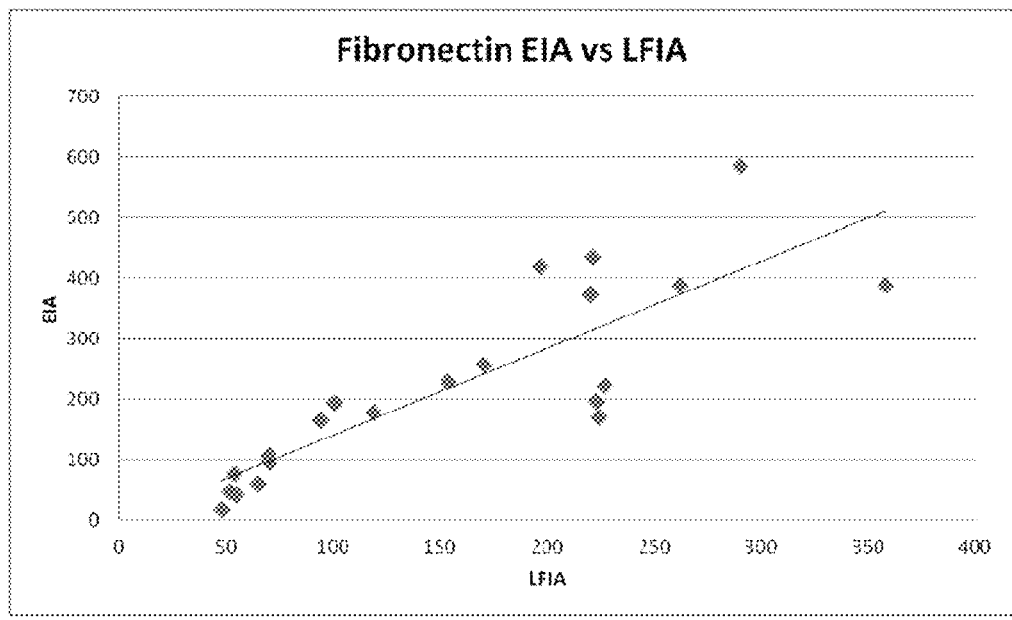
FIG. 9 is a graph illustrating a comparison of the results of a fibronectin ELISA with the results of a FN-LFIA test, in accordance with various embodiments.

Following completion of the capillary migration, the device was scanned, and the amount of fibronectin in the sample was determined by quantitative densitometry relative to a standard curve using purified fibronectin as standard. FIG. 9 is a graph illustrating a comparison of the results of a fibronectin ELISA with the results of the FN-LFIA test described above. As can be seen in FIG. 9, the results of the two tests corresponded with one another quite closely, indicating that the FN-LFIA test is sensitive and accurate.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A method for determining if a subject has gestational diabetes, comprising:
   providing a test sample from the subject;
   measuring a level of glycosylated fibronectin in the sample;
   measuring a level of glycosylated PSG in the sample;
   determining whether the level of glycosylated fibronectin and the level of glycosylated PSG is elevated in the sample relative to a control, wherein a determination that the level of glycosylated fibronectin and the level of glycosylated PSG is elevated in the sample indicates that the subject has gestational diabetes.

2. The method of claim 1, wherein measuring a level of glycosylated fibronectin in the sample comprises detecting glycosylated fibronectin using an antibody.

3. The method of claim 2, wherein the antibody is an anti-fibronectin-SNA antibody.

4. The method of claim 1, wherein measuring a level of glycosylated pregnancy-specific glycoprotein (PSG) in the sample comprises detecting glycosylated PSG using an antibody.

5. The method of claim 4, wherein the antibody is an anti-PSG-AAL antibody.

6. The method of claim 1, wherein the method further comprises measuring adiponectin, sex hormone binding globulin (SHBG), C-reactive protein (CRP), a ratio of human chorionic gonadotropin (hCG) to placental lactogen, or a combination thereof in the sample.

7. The method of claim 6, wherein method further comprises measuring two or more of the group consisting of adiponectin, sex hormone binding globulin (SHBG), C-reactive protein (CRP), a ratio of human chorionic gonadotropin (hCG) to placental lactogen, or a combination thereof in the sample.

8. The method of claim 7, wherein method further comprises measuring three or more of the group consisting of adiponectin, sex hormone binding globulin (SHBG), C-reactive protein (CRP), a ratio of human chorionic gonadotropin (hCG) to placental lactogen, or a combination thereof in the sample.

9. The method of claim 8, wherein method further comprises measuring adiponectin, sex hormone binding globulin (SHBG), C-reactive protein (CRP), and a ratio of human chorionic gonadotropin (hCG) to placental lactogen in the sample.

10. The method of claim 1, wherein the control comprises a reference value.

11. The method of claim 1, wherein the control is a control reference sample from a non-diabetic subject.

12. The method of claim 1, wherein the method comprises determining whether the level of glycosylated fibronectin and the level of glycosylated PSG is elevated in the sample relative to a control.

13. The method of claim 1, wherein the method further comprises determining whether a level of C-reactive protein (CRP) and/or a ratio of human chorionic gonadotropin (hCG) to placental lactogen is elevated in the sample relative to a control.

14. The method of claim 1, wherein the method further comprises determining whether adiponectin and/or sex hormone binding globulin (SHBG) are decreased in the sample relative to a control.

15. The method of claim 1, wherein an elevation relative to the control in the level of glycosylated fibronectin and/or the level of glycosylated PSG in the sample indicates that the subject has gestational diabetes.

16. The method of claim 15, wherein an elevation relative to the control in the level of glycosylated fibronectin and the level of glycosylated PSG in the sample indicates that the subject has gestational diabetes.

17. The method of claim 16, wherein the method further comprises determining whether a level of C-reactive protein (CRP) and/or a ratio of human chorionic gonadotropin (hCG) to placental lactogen is elevated in the sample relative to a control, and wherein an elevation relative to the control of the level of C-reactive protein (CRP) and/or a ratio of human chorionic gonadotropin (hCG) to placental lactogen.

18. The method of claim 16, wherein the method further comprises wherein the method further comprises determining whether adiponectin and/or sex hormone binding globulin (SHBG) are decreased in the sample relative to a control, and wherein a decrease relative to control in the level of adiponectin and/or sex hormone binding globulin (SHBG) indicates that the subject has gestational diabetes.

19. The method of claim 16, wherein the method further comprises determining whether a level of C-reactive protein (CRP) and a ratio of human chorionic gonadotropin (hCG) to placental lactogen are elevated in the sample relative to a control, and determining whether adiponectin and sex hormone binding globulin (SHBG) are decreased in the sample relative to a control, and wherein an elevation relative to the control of the level of C-reactive protein (CRP) and/or a ratio of human chorionic gonadotropin (hCG) to placental lactogen, or a decrease relative to control in the level of adiponectin and/or sex hormone binding globulin (SHBG) indicates that the subject has gestational diabetes.

20. The method of claim 19, wherein the increase or decrease relative to the control is at least 10%.

21. The method of claim 1, wherein the level of glycosylated fibronectin and/or the level of glycosylated PSG in the sample is determined using a lateral flow device.

22. A kit for carrying out the method of claim 1, the kit comprising an antibody specific for glycosylated fibronectin and an antibody specific for glycosylated PSG and instructions for using the kit.

23. The method of claim 1, wherein the test sample comprises whole blood, serum, or saliva.

24. The method of claim 1, wherein the level of glycosylated fibronectin and/or the level of glycosylated PSG in the sample is determined using an ELISA assay.

* * * * *